United States Patent [19]

Shibata et al.

[11] Patent Number: 5,708,370
[45] Date of Patent: Jan. 13, 1998

[54] DEPTH SENSOR WHICH DETECTS GRINDING DEPTH BY MEANS OF CHANGE AND RESISTANCE OF RESISTOR ALSO GROUND DURING GRINDING

[75] Inventors: Takuji Shibata; Takashi Watanabe, both of Miyagi, Japan

[73] Assignee: Sony Corporation, Tokyo, Japan

[21] Appl. No.: 638,182

[22] Filed: Apr. 26, 1996

[30] Foreign Application Priority Data

Apr. 28, 1995 [JP] Japan .................. 7-106394

[51] Int. Cl.$^6$ ........................................ G01N 27/04
[52] U.S. Cl. .............................. 324/699; 73/7
[58] Field of Search ................... 73/7, 699, 226, 73/229, 657, 71.1, 71.2, 71.5, 207.16, 207.19

[56] References Cited

U.S. PATENT DOCUMENTS 5,056,353 10/1991 Matono ............................... 73/7
5,057,956 10/1991 Muratomi et al. .
5,132,617 7/1992 Leach ........................... 324/207.16
5,559,429 9/1996 Mowry ............................. 324/699

FOREIGN PATENT DOCUMENTS

0 466 159 1/1992 European Pat. Off. .
2 424 106 12/1975 Germany .

Primary Examiner—Christine K. Oda
Attorney, Agent, or Firm—Hill, Steadman & Simpson

[57] ABSTRACT

A depth sensor for detecting a depth, when grinding the magnetic head in order to set the depth of the magnetic head to a predetermined length including an analog sensor having a resistor whose resistance changed continuously by being ground together with the magnetic head when grinding the magnetic head in a depth direction and for detecting the depth from said continuously changed resistance, and a digital sensor having a resistor whose resistance is changed non-continuously by being ground together with the magnetic head when grinding the magnetic head in the depth direction and for detecting the depth from the non-continuously changed resistance.

8 Claims, 7 Drawing Sheets

DEPTH SENSOR WHICH DETECTS GRINDING DEPTH BY MEANS OF CHANGE AND RESISTANCE OF RESISTOR ALSO GROUND DURING GRINDING

BACKGROUND OF THE INVENTION

1. Field of the Invention

The present invention relates to a depth sensor for detecting depth amount when manufacturing a magnetic head. In detail, the depth sensor in accordance with the present invention can detect the depth amount accurately by comprising both an analog sensor and a digital sensor.

2. Description of the Related Arts

In a field of a magnetic recording equipment such as a hard disk equipment and the like, it is required to make the equipment smaller and to make its capacity larger. Accordingly, it is desired for a magnetic head to make a line recording density higher and to make a track narrower. Recent attention has been directed to a magnetic resistance effect type magnetic head (hereafter, referred to as an MR head). Each a magnetic head is advantageous in making the line recording density higher and in making the track narrower. The MR head detects a resistance change of the MR film due to a signal magnetic field from a recording medium as a reproducing output by using a magnetic resistance effect film (hereafter, referred to as an MR film) whose resistance is changed based on a strength of a magnetic field.

In the MR film used in such an MR head, when the resistance is small, changing amount of the resistance associated with the change of an outer magnetic field becomes small. Thus, when the resistance of the MR film is small, the reproducing output from the MR head is reduced. As a result, it is necessary to make the resistance of the MR film larger in a case of the MR head.

Incidentally, such an MR head is classified into a transverse type MR head and a longitudinal type MR head.

Figure 6:
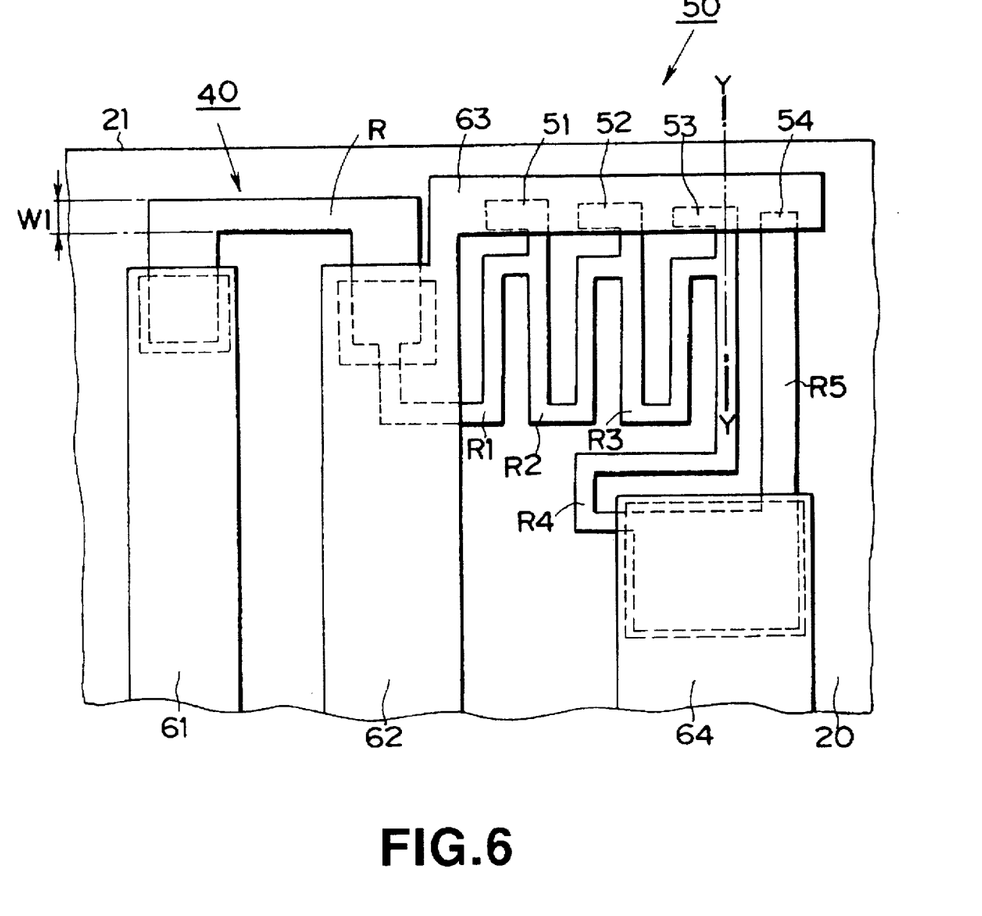
FIG. 6 is an enlarged main portion plan view showing in an enlarged form the depth sensor shown in FIG. 3.

The transverse type MR head is, as shown in FIG. 6, such that an MR film 101 is arranged parallel to a moving direction M1 of the recording medium and electrodes 102, 103 are fixed in left and right sides of this MR 101. At this time, a resistance R of the MR film 101 is represented by $R=(\rho \times T)/(W \times t)$, where $\rho$, W, T, t are a specific resistance, a width, a length and a thickness of the MR film 101 respectively. Thus, in the transverse type MR head, when the track is made narrower, the length T of the MR film 101 becomes short. Then, if the width W and thickness T of the MR film 101 are unchanged, the resistance of the MR film 101 is reduced, and thereby the reproducing output is reduced. Specifically, for example, the width W of the MR film 101 must be set equal to or more than 1.5 μm in order to obtain the reproducing output having the same level as the transverse type MR head having a wide track with a length T of 4 μm and a width W of 3 μm in the transverse type MR head having a narrow track with a length T of 2 μm. In this way, in a case of the transverse type MR head, in order to make the track narrower while maintaining the reproducing output, it is necessary to form the whole shape of the MR film 101 more minute.

Figure 7:
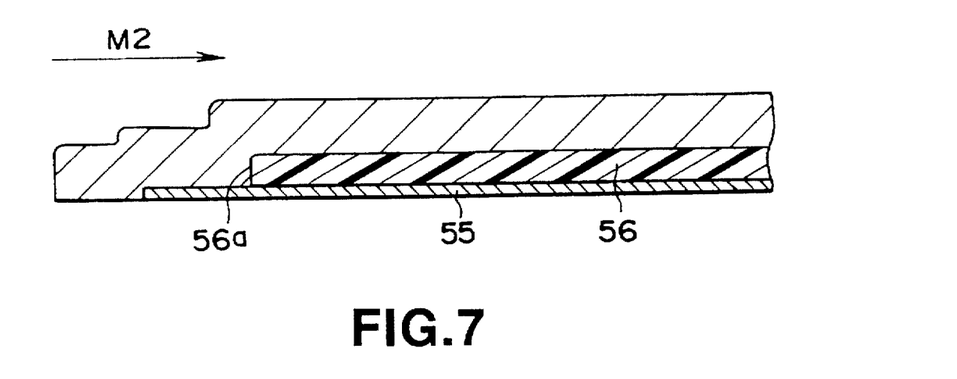
FIG. 7 is a transverse section view showing a digital sensor portion of the depth sensor, cut in a plane along a line Y—Y, shown in FIG. 6.

On the other hand, the longitudinal type MR head is, as shown in FIG. 7, composed of the MR film 101 arranged vertically in the moving direction M1 of the recording medium and the electrodes 102, 103 fixed in upper and lower portions of this MR 101. Accordingly, it is possible to make the reproducing output higher and make the track narrower without forming the whole shape of the MR film 101 minutely. That is, in a case of the longitudinal type MR head, if the width W of the MR film 101 is made narrower in order to make the track narrower, the resistance R of the MR film 101 is increased. This enables the reproducing output to be larger.

In such a longitudinal type MR head, an end of the MR film 101 on a side closer to the recording medium, that is, an MR film tip portion 111 is covered with the electrode, and further an end of the MR film 101 on a side farther from the recording medium, that is, an MR film tail portion 112 is covered with the electrode. A portion between the MR film tip portion 111 and the MR film tail portion 112, that is, a portion which is not covered with the electrode is a magnetic sensing portion of the MR film. Since the MR film tip portion 111 and the MR film tail potion 112 are covered with the electrode, they do not contribute to the reproducing output. Thus, when a length of the portion which is covered with the electrode of the MR film tip portion 111, that is, a depth dp is long, a distance between the recording medium and the magnetic sensing portion becomes long whereby the reproducing output is reduced. For this reason, in the longitudinal type MR head, it is necessary to make the depth dp as short as possible. In current situation, it is required to make the depth approximate 0.5+ and −0.2 μm. Further, It is anticipated that the depth will be required to be more shorter in future.

Incidentally, in a case of the above mentioned longitudinal type MR head, at first, the longitudinal type MR head is manufactured while the depth is set longer than a desired depth length. After that, it is manufactured such that a portion of a side of the recording medium is ground until the depth reaches the desired length. When grinding the portion of the side of the recording medium of the longitudinal type MR head as mentioned above, naturally it is necessary to grind while detecting a degree of the depth in a grinding process.

However, as mentioned above, since the depth is very short, it is very difficult to detect the depth in the grinding process. Then, a depth sensor which can detect the depth accurately is required when grinding the portion of the side of the recording medium of the longitudinal type MR head.

The present invention is proposed in view of the conventional circumstances. It is therefore an object of the present invention to provide a depth sensor which can a depth accurately when manufacturing a longitudinal type MR head.

SUMMARY OF THE INVENTION

A depth sensor according to the present invention designed to attain the above mentioned object is for detecting a depth length, when grinding a magnetic head in order to set the depth of the magnetic head to a predetermined length. The depth sensor is characterized by comprising analog sensor having a resistor whose resistance is changed continuously by ground with the magnetic head when grinding the magnetic head and for detecting the depth from the continuously changed resistance as mentioned above, and a digital sensor having a resistor whose resistance is changed non-continuously by ground with the magnetic head when grinding the magnetic head and for detecting the depth from the non-continuously changed resistance as mentioned above.

FUNCTION

The depth sensor in accordance with the present invention detects the depth gradually and roughly by using the digital sensor, and detects the depth continuously and accurately by using the analog sensor.

That is, the digital sensor can know the depth in each of stages in which the resistance of the digital sensor is changed non-continuously, by relating in advance the depth to a case when the resistance of the digital sensor is changed non-continuously. However, since the digital sensor can get only the depth in each of the stages in which the resistance of the digital sensor is changed non-continuously, the depth is detected gradually and roughly as a result.

On the other hand, in the analog sensor, at first, a relation between a change of the resistance of the analog sensor and a change of the depth is investigated based on a result detected by the digital sensor. That is, it is possible to find out the relation between the change of the resistance of the analog sensor and the change of the depth, based on the resistance of the analog sensor in each of the stages in which the resistance of the digital sensor is changed, and the depth detected at that time by the digital sensor. If the relation between the change of the resistance of the analog sensor and the change of the depth becomes clear in this way, the depth can be detected continuously and accurately from the resistance of the analog sensor.

Further objects and advantages of the present invention will be apparent from the following descriptions of the preferred embodiment of the invention as illustrated in the accompanying drawings.

DESCRIPTION OF THE PREFERRED EMBODIMENT

An specific embodiment in accordance with the present invention will be explained hereafter in detail with reference to the drawings. Since the embodiment described below is a preferred embodiment of the present invention, various limitations which are technically preferred are imposed on the embodiments. However, the range of the present invention is not limited to the embodiment, unless there are descriptions in which the present invention is limited especially in the following explanation.

Figure 1:
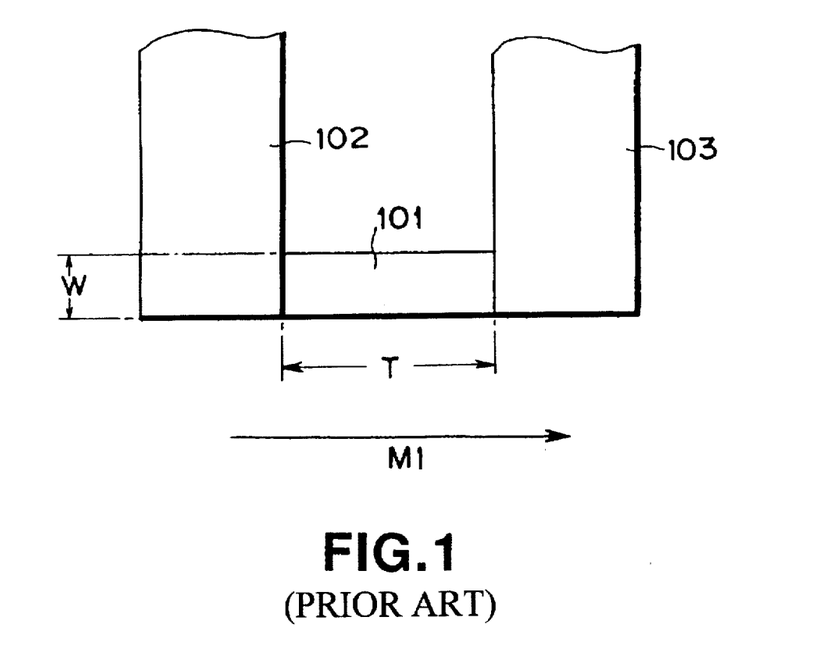
FIG. 1 is a main portion diagram view showing one example of a conventional transverse type MR head.
Figure 2:
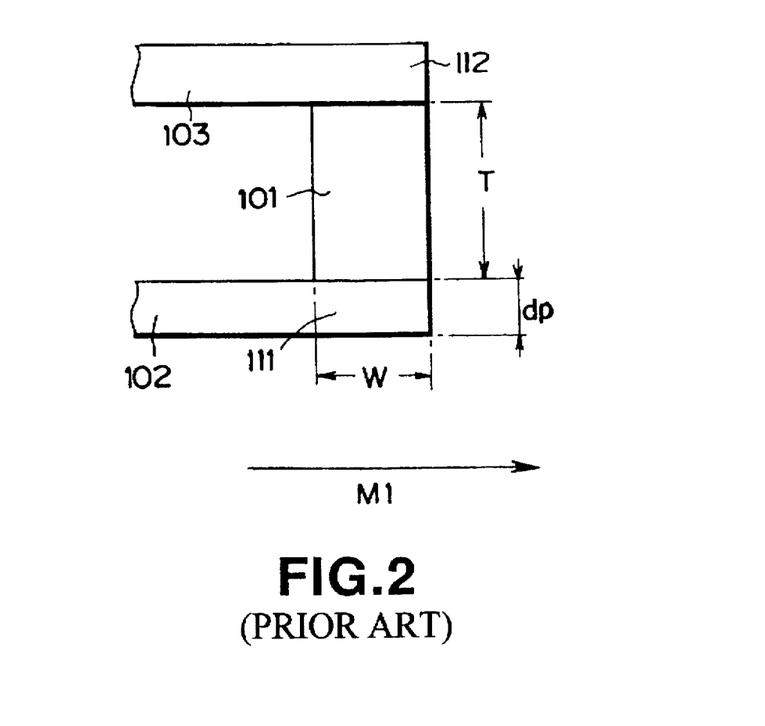
FIG. 2 is a main portion diagram view showing one example of a conventional longitudinal type MR head.
Figure 3:
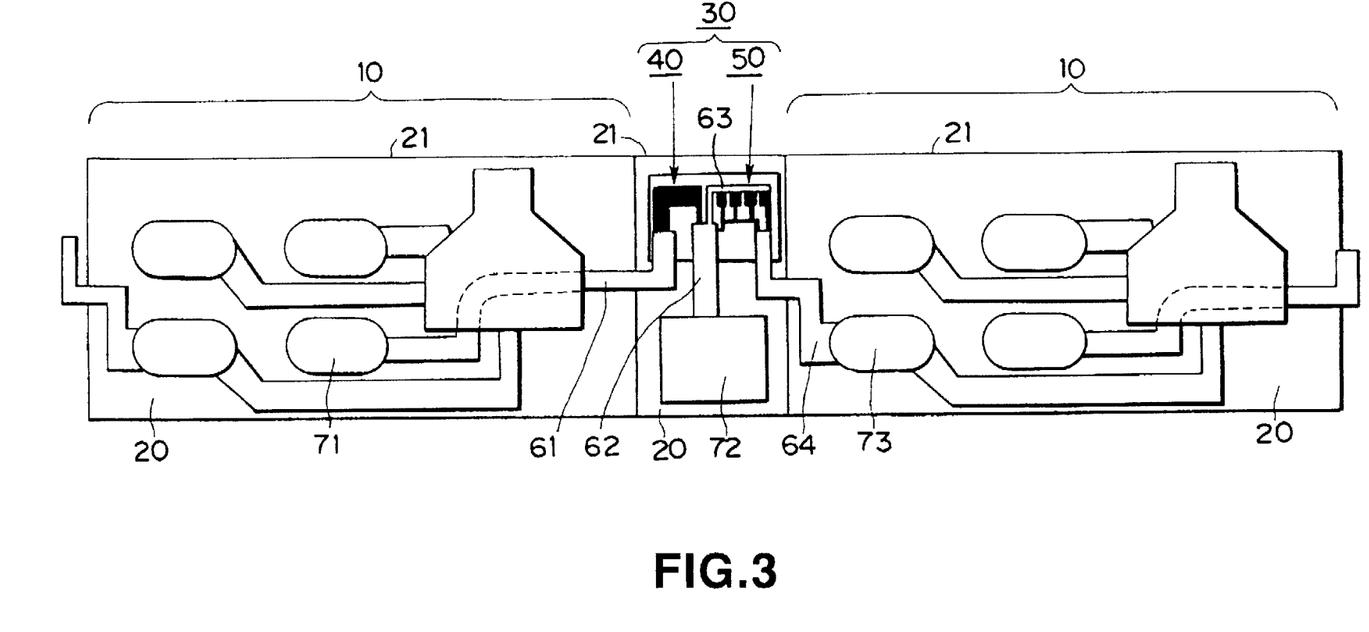
FIG. 3 is a top plan view showing one example of a depth sensor in accordance with the present invention.

A depth sensor in this embodiment detects a depth of a longitudinal type MR head formed on a board in a thin film process. As shown in FIG. 3, the depth sensor is formed with MR heads 10 in the thin film process, when the MR heads 10 are formed on a base 20 which is identical with the MR heads 10. Now, a plurality of MR heads 10 are formed unitedly on the base 20, as shown in FIG. 3. A depth sensor 30 is formed between these MR heads 10. When the depth sensor 30 is formed on the base 20 which is identical with the MR heads 10 as mentioned above, the depth sensor 30 can be formed with the MR heads 10, and thereby the depth sensor 30 can be formed without nearly adding a new process. Further, the depth sensor 30 is formed between the MR head 10 and the MR head 10 in this way, a wiring of the depth sensor 30 is connected to those of the MR heads 10 as described later, and respective terminals are used in common. Accordingly, an occupied area of the depth sensor 30 on the board becomes small so that more MR heads 10 can be obtained from one board 20.

When the MR heads are facilitated, the MR heads 10 formed on the board 20 and the depth sensor 30 are ground gradually from an end plane 21 of the board 20 such that the depth becomes shorter, while detecting the depth of the MR head 10 by means of the depth sensor 30. And, the depth of the MR head 10 is set to a predetermined length. (Hereafter, this process is referred to as a grinding process. After the depth is set to the predetermined length, a plurality of MR heads 10 formed on the board are cut out respectively, and the MR heads are completed.

The depth sensor 30 for detecting the depth of the MR head 10 in this way, as shown in FIG. 3, comprises an analog sensor 40 for detecting the depth continuously and a digital sensor 50 for detecting the depth non-continuously. The analog sensor 40 and the digital sensor 50 are formed on the board 20 so as to be adjacent to each other. This analog sensor 40 is ground with the MR heads 10 in the grinding process, and has a resistor whose resistance is changed continuously. The depth is detected from the continuously changed resistance. The digital sensor 50 is ground with the MR heads 10 in the grinding process, and has a resistor whose resistance is non-continuously changed. The depth is detected from the non-continuously changed resistance. Wirings 61, 62, 63 and 64 intended to detect the respective resistances are supplied from the analog sensor 40 and the digital sensor 50.

Figure 4:
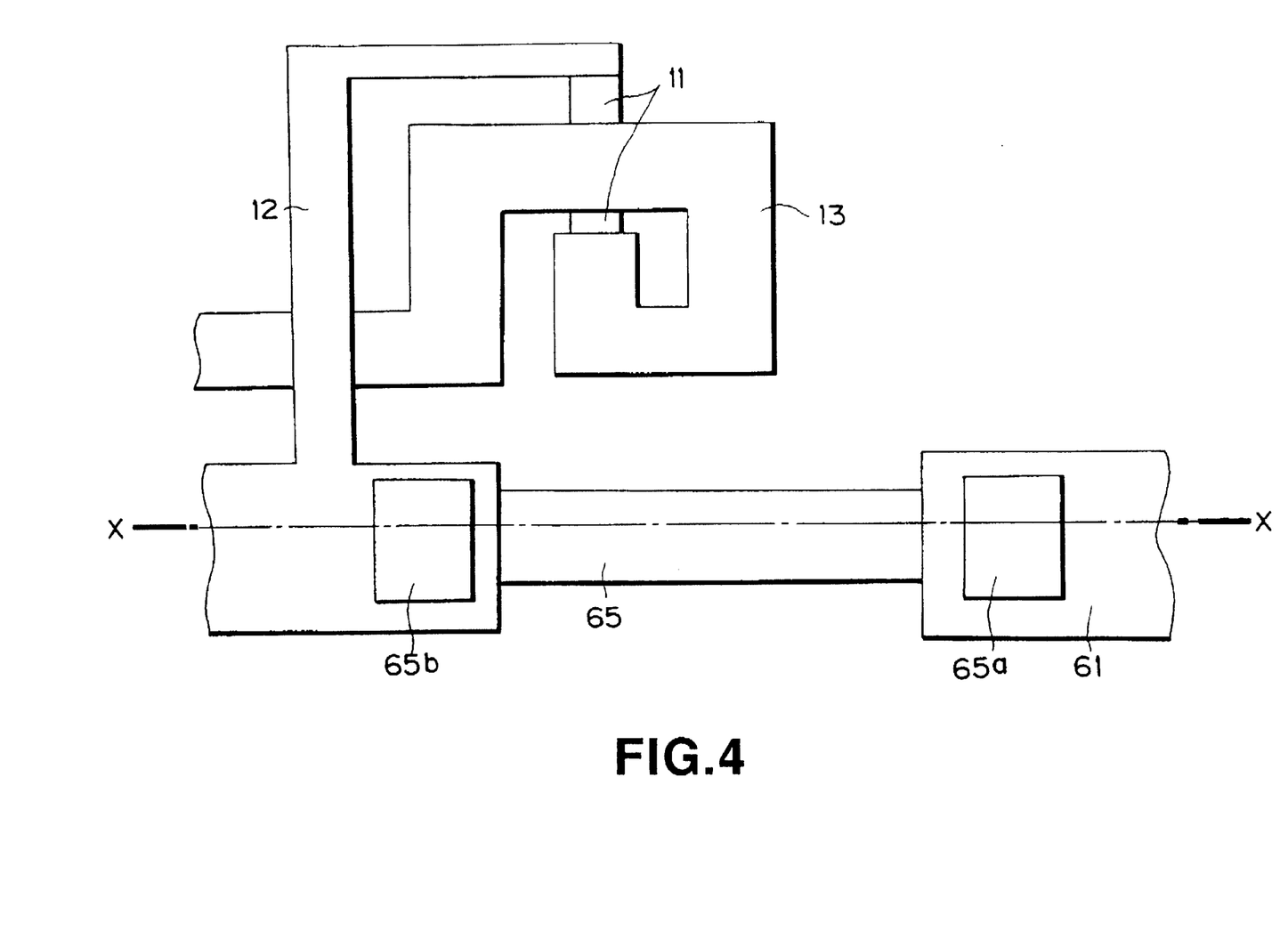
FIG. 4 is a main portion diagram view showing a wiring block of an MR head and the depth sensor.
Figure 5:
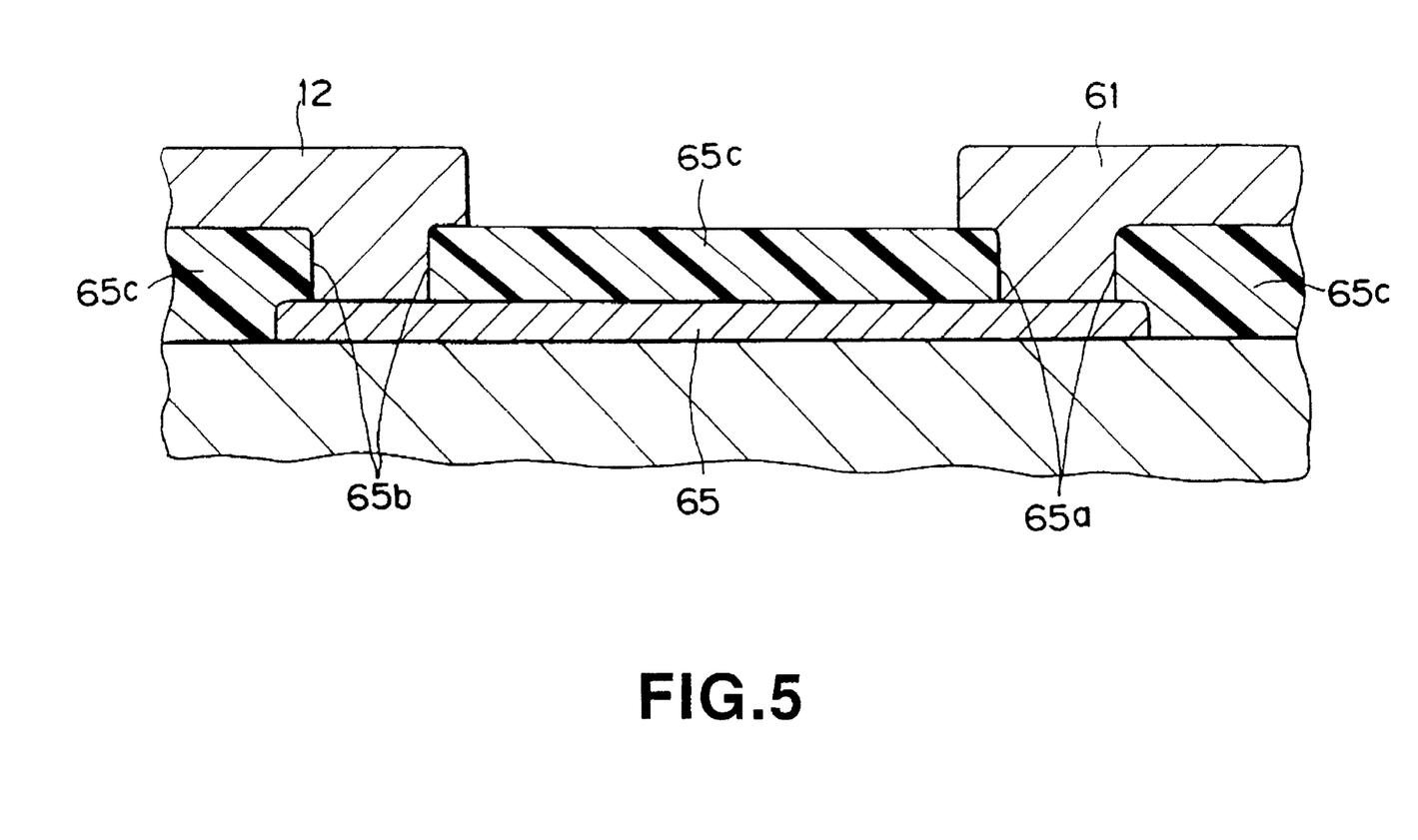
FIG. 5 is a transverse section view taken along a line X—X in the wiring block shown in FIG. 4.

Now, one wiring 61 of the wirings from the analog sensor 40, as shown in FIG. 4, is connected to a wiring 12 from an MR film 11 of the MR head 10 through a thin film conductor 65. The thin film conductor 65 is formed simultaneously with the other wiring 13 supplied from the MR film 11, connected to a wiring 61 from the analog sensor in a connecting hole 65a, and connected to the wiring 12 from the MR film 11 in a connecting hole 65b. That is, as shown in FIG. 5, an insulation layer 65c is formed on the thin film conductor 65. The connecting holes 65a, 65b are formed in two positions on the insulation layer 65c. The thin film conductor 65, and the wiring 61 formed as a different layer from the thin film conductor 65 are connected to each other in the connecting hole 65a. The thin film conductor 65, and the wiring 12 formed as a different layer from the thin film conductor 65 are connected to each other in the connecting hole 65b.

As mentioned above, since the wiring 61 from the analog sensor 40 is connected to the wiring 12 from the MR film 11 of the MR head 10 through the thin film conductor 65, the terminal intended to pick up a signal from the analog sensor 40 and the terminal of the MR head 10 can be integrated into a common terminal 71, as shown in FIG. 3. In addition, since the thin film conductor 65, the wiring 61 from the analog sensor 40 connected to the thin film conductor 65, and the wiring 12 from the MR film 11 are formed as the different layers, it is possible to simultaneously form the thin film conductor 65 and the other wiring 13 from the MR film 11, as mentioned above. As a result, the thin film conductor 65 can be formed without adding a new process to the thin film process.

Incidentally, only the wiring with respect to the MR head 10 is shown as that of a magnetic head in FIGS. 4 and 5. However, it is allowable that the magnetic head is a laminated type magnetic head in which the magnetic head for recording is laminated on the MR head. In a case where the magnetic head for recording is laminated in this way, a wiring of the magnetic head for recording is formed additionally on the wiring shown in FIGS. 4 and 5.

On the other hand, the other wiring 62 from the analog sensor 40 is connected to the wiring 63 from the digital sensor 50, as shown in FIG. 3. Thus, the terminal from this wiring 62 is used as a terminal 72 common to the terminal of the digital sensor 50.

The one wiring 63 of the wirings 63, 64 from the digital sensor 50 is connected to the wiring 62 from the analog sensor 40 as mentioned above. The terminal from this wiring 63 is used as the terminal 72 common to the terminal of the analog sensor 40. The other wiring 64 is supplied without connected to the analog sensor 40, and a terminal 73 is formed at an end thereof. However, this terminal 73 need not be an independent terminal. For example, it is allowable that the terminal 73 is used in common with the terminal of the magnetic head for recording laminated on the MR head, as shown in FIG. 3.

The analog sensor 40 and digital sensor 50 of the depth sensor 30 as mentioned above will be explained hereinafter in more detail.

A resistor portion of the analog sensor 40 is formed in the same film thickness as that of the MR film 11 by means of a NiFe thin film which has the same material as that of the MR film 11. In this way, assuming that the resistor portion of the analog sensor 40 has the same material and the same film thickness as those of the MR film 11, since the analog sensor 40 and the MR head 10 are ground similarly in the grinding process, this improves an accuracy of the analog sensor 40.

This NiFe thin film is arranged approximately parallel to the end plane 21 in the vicinity of the end plane 21 of the board 20, as shown in FIG. 6. The wirings 61, 62 are supplied from the both ends thereof. The portion between these wirings 61, 62 is a resistor R. These wirings 61, 62 are intended to pick up the signal from the analog sensor 40, and composed of thin film conductors. As mentioned above, the one wiring 61 is connected to the wiring 12 from the MR film 11, extending to the terminal 71 common to the MR head 10. The other wiring 62 is connected to the wiring 63 from the digital sensor 50, extending to the terminal 72 common to the digital sensor 50. The resistor R arranged approximately parallel to the end plane 21 in the vicinity of the end plane 21 of the board 20 is gradually narrow in a width W1 as the grinding proceeds in the grinding process and thereby the resistance thereof is increased gradually. Thus, in the analog sensor 40, if a relation between a change of this resistance and the grinding progress is clear, it is possible to find out the degree of the grinding progress by measuring this resistance.

On the other hand, a resistor portion of the digital sensor 50 is formed in the same film thickness as the MR film 11 by means of the NiFe thin film which has the same material as the MR film 11, similarly to the analog sensor 40. In this way, assuming that the resistor portion of the digital sensor 50 has the same material and the same film thickness as those of the MR film 11, the digital sensor 50 and the MR head 11 are ground similarly in the grinding process so that this improves an accuracy of the digital sensor 50.

This NiFe thin film is patterned such that a first end 51, a second end 52, a third end 53 and a fourth end 54 are formed in the vicinity of the end plane 21 of the board 20, as shown in FIG. 6. These ends 51, 52, 53 and 54 are respectively connected to the wiring 63. This wiring 63 is intended to pick up a signal from the digital sensor 50, composed of the thin film conductors, as mentioned above, connected to the wiring 62 of the analog sensor 40, and extended to the terminal 72 common to the analog sensor 40.

The NiFe thin film is patterned so as to link between the first end 51 and the wiring 62, between the first end 51 and the second end 52, between the second end 52 and the third end 53, between the third end 53 and the wiring 64 and between the fourth end 54 and the wiring 64. The wiring 64 connected to the third end 53 and the fourth end 54 is intended to pick up the signal from the digital sensor 50, composed of the thin film conductors, and extended to the terminal 73 for the digital sensor, as mentioned above. Thus, the NiFe thin film between the first end 51 and the wiring 62 is a first resistor R1, the NiFe thin film between the first end 51 and the second end 52 is a second resistor R2, the NiFe thin film between the second end 52 and the third end 53 is a third resistor R3, the NiFe thin film between the third end 53 and the wiring 64 is a fourth resistor R4, and the NiFe thin film between the fourth end 54 and the wiring 64 is a fifth resistor R5.

The first to fourth ends 51, 52, 53 and 54 are formed when the depth portion of the MR head 10 is formed, similarly to the depth portion of the MR head 10. That is, when these ends 51, 52, 53 and 54 are formed, similarly to the MR head 11, as shown in FIG. 7, at first, a NiFe thin film 55 is formed, next, an insulation layer 56 is formed on this NiFe thin film, and a tip portion of this insulation layer 56 is removed. Then, the wiring 63 composed of the thin film conductors is formed on the NiFe thin film 55 and the insulation layer 56. In the thus-formed ends 51, 52, 53 and 54, the NiFe thin film 55 and the wiring 63 are connected electrically to each other before the grinding process, but disconnected from each other, when the grinding proceeds to a tip portion 56a on the insulation layer 56, as the grinding is carried out gradually as shown in an arrow M2 of FIG. 7 in the grinding process. Thus, in the digital sensor 50, it is possible to judge whether or not the grinding is carried out up to a position of the tip portion 56a of the insulation layer 56, based on a change of a conductive state between the NiFe thin film 55 and the wiring 63. In the digital sensor 50, each of the ends 51, 52, 53 and 54 is formed such that the tip portion 56a on the insulation layer 56 is located differently in each of the ends 51, 52, 53 and 54 so as to make such a judgment gradually.

Figure 8:
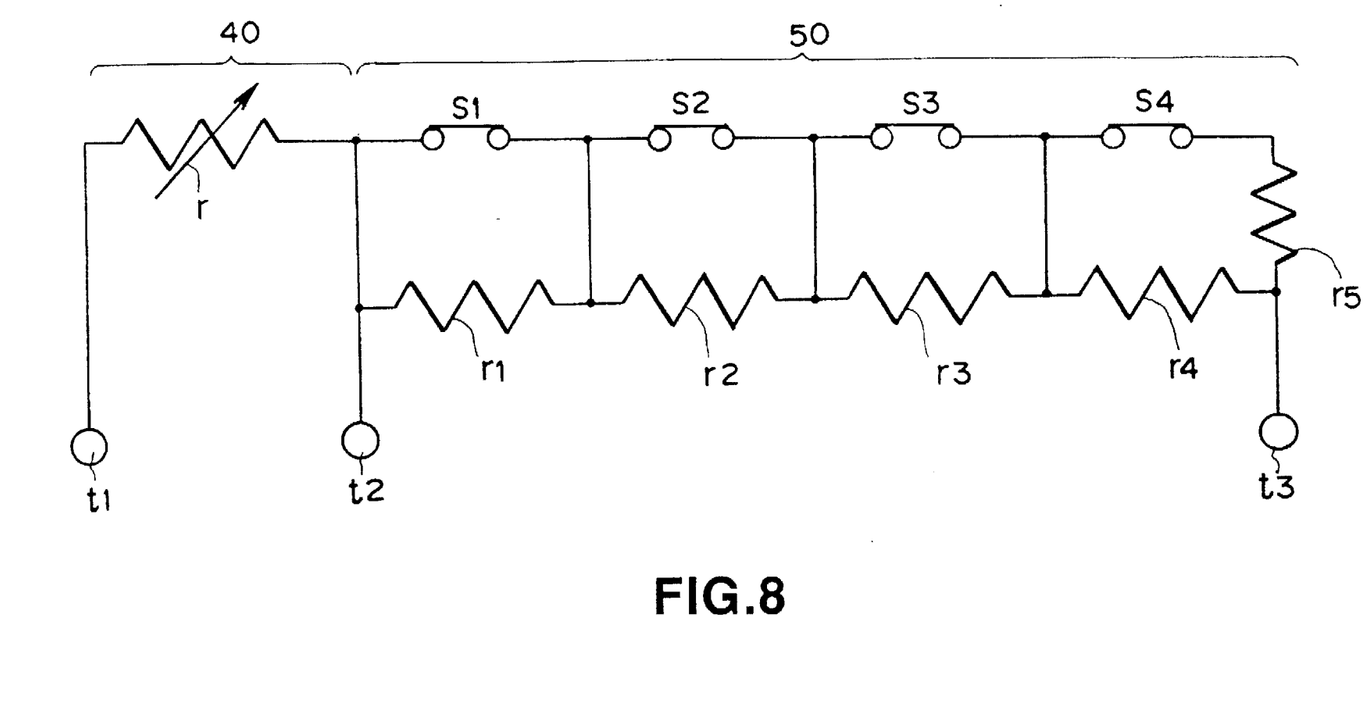
FIG. 8 is an equivalent circuit diagram of the depth sensor shown in FIG. 6.

FIG. 8 shows an equivalent circuit diagram of the analog sensor 40 and the digital sensor 50, as mentioned above. That is, the analog sensor 40 comprises a variable resistance r corresponding to the resistor R, and terminals t1, t2 respectively corresponding to the terminals 71, 72. A resistance of the variable resistor r is increased gradually as the grinding proceeds in the grinding process. Accordingly, in the analog sensor 40, the grinding progress can be detected continuously by measuring a resistance Ra of this variable resistor r. On the other hand, the digital sensor 50 comprises five resistors r1, r2, r3, r4 and r5 respectively corresponding to the resistors R1, R2, R3, R4 and R5, four switches s1, s2, s3 and s4 respectively corresponding to the first to fourth ends 51, 52, 53 and 54, and terminals t2, t3 respectively corresponding to the terminals 72, 73. These switches s1, s2, s3 and s4 are turn off sequentially as the grinding proceeds in the grinding process. Accordingly, in the digital sensor 50, it is possible to detect the grinding progress gradually by measuring a resistance Rd of such a whole circuit.

Detecting of the depth by means of the depth sensor 40 as mentioned above will be hereinafter explained more specifically.

When the depth is detected in the grinding process, the signal from the analog sensor 40 is picked up from the terminals 71, 72. Then, the resistance Ra of the resistor R in the analog sensor 40 is monitored. Further, the signal from the digital sensor 50 is picked up from the terminals 72, 73. Then, the resistance Rd of the whole circuit in the digital sensor 50 is monitored.

Figure 9:
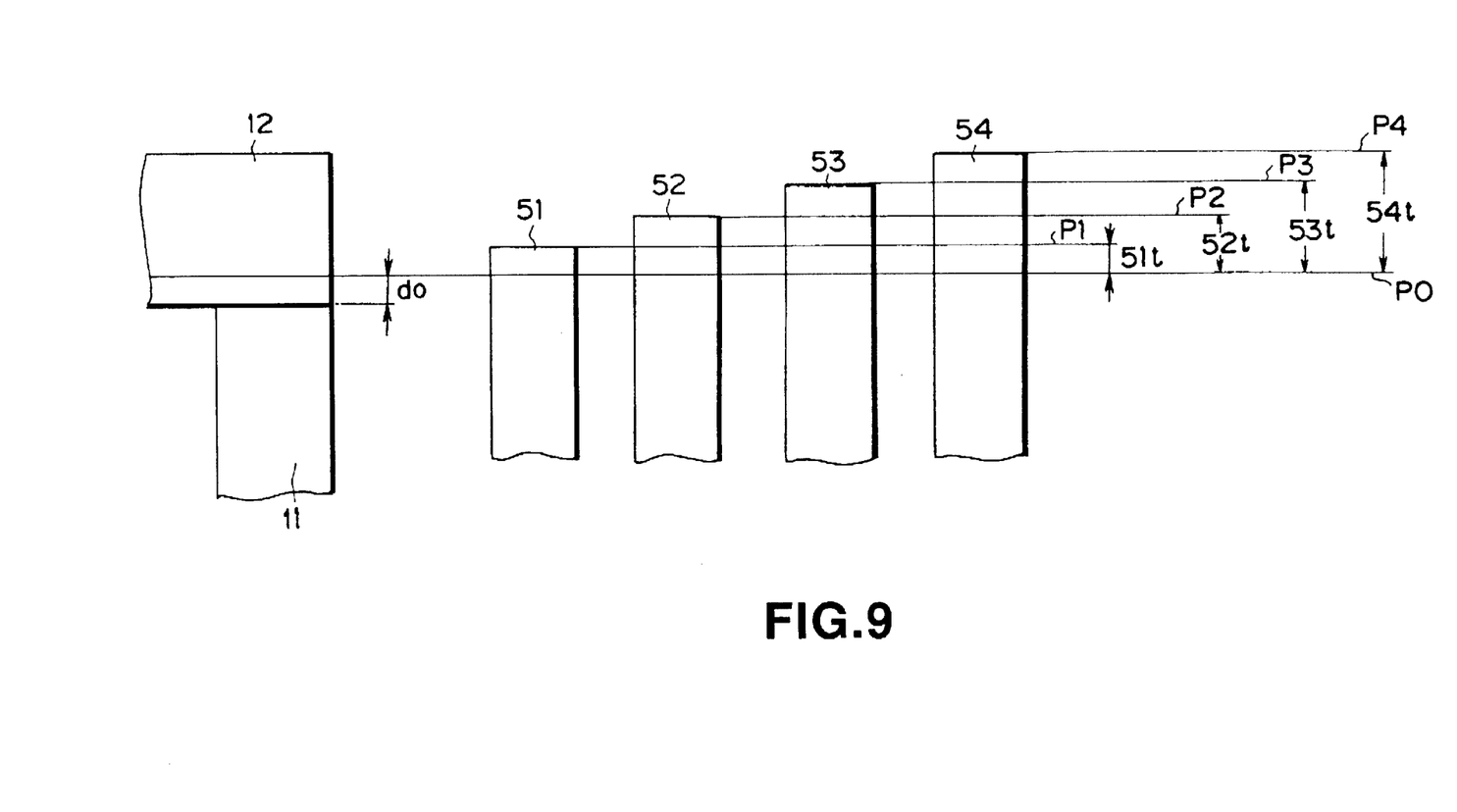
FIG. 9 is a top plan view showing one example of an end of a digital sensor.

By the way, the digital sensor 50 is formed, as shown in FIG. 9, in the following manner. That is, a length 51t between a position P0 having a desired depth d0 and a position P1 at the tip portion of the insulation layer in the first end 51 is 0.25 μm. A length 52t between the position P0 having a desired depth dp and a position P2 at the tip portion of the insulation layer in the second end 52 is 0.75 μm. A length 53t between the position P0 having the desired depth dp and a position P3 at the tip portion of the insulation layer in the third end 53 is 1.5 μm. And, a length 54t between the position P0 having a desired depth 2 dp and a position P4 at the tip portion of the insulation layer in the fourth end 54 is 3.0 μm. Further, the first to fifth resistors R1, R2, R3, R4 and R5 in the digital sensor 60 are formed such that they have sufficiently large resistances so as to detect the resistances with high sensitivity.

At this time, assuming that d0 is the desired depth, D1 is a resistance of the first resistor R1 in the digital sensor 50, D2 is a resistance of the second resistor R2 in the digital sensor 50, D3 is a resistance of the third resistor R3 in the digital sensor 50, D4 is a resistance of the fourth resistor R4 in the digital sensor 50 and D5 is a resistance of the fifth resistor R5 in the digital sensor 50, then a relation between the depth d in the grinding processing and the resistance Rd of the whole circuit in the digital sensor 50 are represented in the following formulas.

When Rd≈D5, d0+3.0 [μm]<d;
When Rd≈D4, d0+1.5 [μm]<d<d0+3.0 [μm];
When Rd≈D3+D4, d0+0.25<d<d0 +0.75 [μm];
When Rd≈D2+D3+D4, d)+0.25<d<d0+0.75 [μm]; and
When Rd≈D1+D2+D3+D4, d<d0+0.25 [μm].

Thus, if monitoring the resistance Rd of the whole circuit in the digital sensor 50 in the grinding process, it is possible to detect the depth d gradually in the grinding processing, until the state of d≈d0+0.25 [μm].

In this way, when gradually detecting the depth d in the grinding processing by using the digital sensor 50, the resistance Ra of the resistor R in the analog sensor 40 is also simultaneously monitored. Then, the relation between the change of the resistance Ra of the resistor R in the analog sensor 40 and the change of the depth d is determined, based on the resistance Ra of the analog sensor 40 in each of stages in which the resistance Rd of the digital sensor 50 is changed and the depth d detected at that time by the digital sensor 50.

In the grinding process when the depth d in the grinding processing is equal to or less than d0+0.25 [μm], the depth d in the grinding processing is monitored, by using the analog sensor 40 in which the relation between the change of the resistor Ra of the resistance R and the change of the depth d is evident as described above. At this time, since the relation between the change of the resistance Ra of the resistor R and the change of the depth d becomes clear, the analog sensor 40 can detect the depth d continuously and accurately from the resistance Ra of the resistor R in the analog sensor 40. Thus, while detecting the depth continuously and accurately by means of the analog sensor 40, the grinding process is carried out until the depth reaches the desired length.

In this way, in the grinding process, at first, the digital sensor 50 detects the depth d gradually and roughly. Next, the analog sensor 40 detects the depth d continuously and minutely. Thus, the depth d can be detected accurately. As a result, it is possible to accurately set the depth to a desired length by using the depth sensor in accordance with the present invention in the grinding process.

Incidentally, although the four ends 51, 52, 53 and 54 are provided in the digital sensor as the ends corresponding to the switches in the above mentioned embodiments, it is allowable that these ends are more or less than the above mentioned case. For example, in a case where it is desirable to measure the depth easier, the ends corresponding to such switches are provided less. In a case where it is desirable to measure the depth more minutely, the ends corresponding to such switches are provided more.

ADVANTAGEOUS EFFECT OF THE INVENTION

As can be seen from the above mentioned explanation, in the depth sensor in accordance with the present invention, the digital sensor detects the depth gradually and roughly, and the analog sensor detects the depth continuously and minutely. The depth can be accurately detected as a result.

Many widely different embodiments of the present invention may be constructed without departing from the spirit and scope of the present invention. It should be understood that the present invention is not limited to the specific embodiment described in the specification, except as defined in the appended claims.

What is claimed is:

1. A depth sensor for detecting a depth, when grinding a magnetic head in order to set the depth of the magnetic head to a predetermined length, comprising:

an analog sensor having a resistor whose resistance is changed continuously by being ground together with the magnetic head when grinding the magnetic head in a depth direction and for detecting the depth from said continuously changed resistance; and a digital sensor having a resistor whose resistance is changed non-continuously by being ground together with the magnetic head when grinding the magnetic head in the depth direction and for detecting the depth from said non-continuously changed resistance.

2. A depth sensor as defined in claim 1, characterized by that said magnetic head is a thin film magnetic head formed in a thin film process.

3. A depth sensor as defined in claim 2, characterized by that said analog sensor and said digital sensor are formed on the same plane as a board formed on said thin film magnetic head.

4. A depth sensor as defined in claim 2, characterized by that at least one of a plurality of terminals intended to pick up a signal from said analog sensor and said digital sensor is used in common with one of a plurality of terminals of said magnetic head.

5. A depth sensor for detecting a depth of a thin film magnetic head, when grinding the thin film magnetic head in order to set the depth of the thin film magnetic head formed on a board to a predetermined length, comprising:

an analog sensor having a resistor whose resistance is changed continuously by being ground together with the thin film magnetic head when grinding the thin film magnetic head and for detecting the depth from said continuously changed resistance; and a digital sensor having a resistor whose resistance is changed non-continuously by being ground together with the thin film magnetic head when grinding the thin film magnetic head and for detecting the depth from said non-continuously changed resistance, wherein said analog sensor and said digital sensor are formed on said board in the same thin film process as the thin film magnetic head.

6. A depth sensor as defined in claim 5, characterized in that said thin film magnetic head is a magnetic resistance effect type head.

7. A depth sensor as defined in claim 6, characterized in that said analog sensor and said digital sensor are composed of the same NiFe film as that of said magnetic resistance effect type head.

8. A depth sensor as defined in claim 5, characterized in that at least one of a plurality of wirings from said analog sensor and said digital sensor is used in common with one of wirings from the thin film magnetic head and connected through a thin film conductor formed on another layer of these wirings.

* * * * *